United States Patent [19]
Pappas et al.

[11] Patent Number: 5,171,283
[45] Date of Patent: Dec. 15, 1992

[54] COMPOUND SHAPE ROTATING BEARING

[75] Inventors: Michael J. Pappas, Caldwell; Frederick F. Buechel, South Orange, both of N.J.

[73] Assignee: Biomedical Engineering Trust, S. Orange, N.J.

[21] Appl. No.: 603,269

[22] Filed: Oct. 22, 1990

Related U.S. Application Data

[63] Continuation of Ser. No. 378,244, Jul. 11, 1989, abandoned.

[51] Int. Cl.$^5$ .............................................. A61F 2/38
[52] U.S. Cl. ........................................ 623/20; 623/18
[58] Field of Search ................................. 623/20, 18

[56]           References Cited
        U.S. PATENT DOCUMENTS

| | | | |
|---|---|---|---|
| 4,205,400 | 6/1980 | Shen et al. | 623/18 |
| 4,224,696 | 9/1980 | Murray et al. | 623/20 |
| 4,568,348 | 2/1986 | Johnson et al. | 623/20 |
| 4,634,444 | 1/1987 | Noiles | 623/20 |
| 4,673,408 | 6/1987 | Grobbelaar | 623/20 |
| 4,822,366 | 4/1989 | Bolesky | 623/20 |
| 4,888,021 | 12/1989 | Forte et al. | 623/20 |
| 4,892,547 | 1/1990 | Brown | 623/20 |

FOREIGN PATENT DOCUMENTS

| | | | |
|---|---|---|---|
| 0000739 | 10/1979 | World Int. Prop. O. | 623/20 |
| 8604808 | 8/1986 | World Int. Prop. O. | 623/20 |
| 8702881 | 5/1987 | World Int. Prop. O. | 623/20 |

*Primary Examiner*—Randall L. Green
*Assistant Examiner*—D. Willse
*Attorney, Agent, or Firm*—J. G. Gilfillan, III; J. D. Kaufmann

[57]                ABSTRACT

A prosthetic joint includes a first bearing element which is attached to a first bone and has a substantially flat bearing surface. A second element having a bearing surface is attached to a second bone. A bearing is disposed between the first and second elements. The bearing has a central axis and is defined by a first surface and a second surface. The first surface is substantially flat and is at least partially in contact with the first flat surface of the first element. At least a portion of the second surface is in contact with the surface of the second element. The area of the planform of the first surface of the bearing is smaller than, and dissimilar in shape from, the area of the planform defined by the second surface of the bearing.

11 Claims, 4 Drawing Sheets

FIG. 5
PRIOR ART
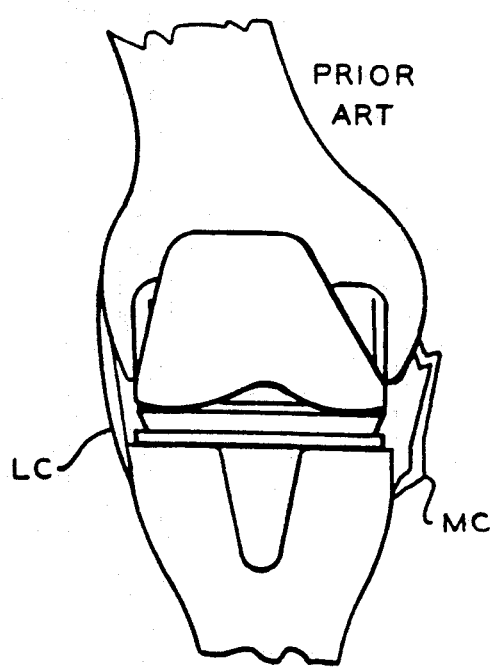
FIG. 6
PRIOR ART
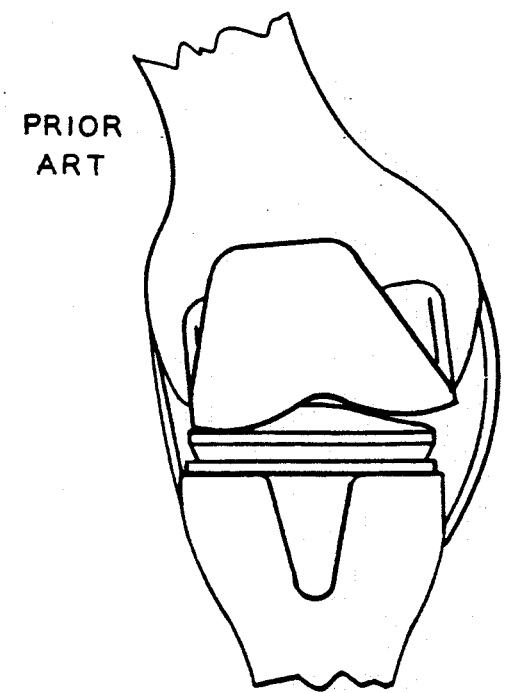
FIG. 9
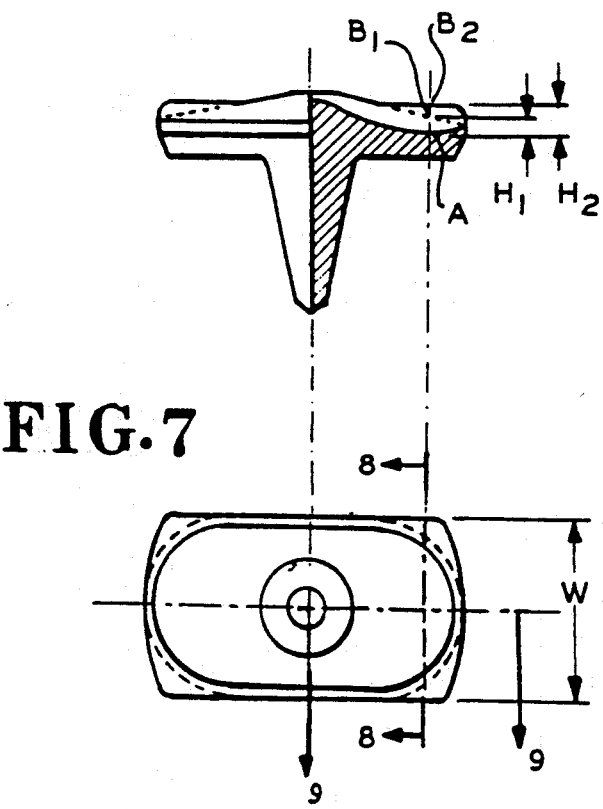
FIG. 7
FIG. 8
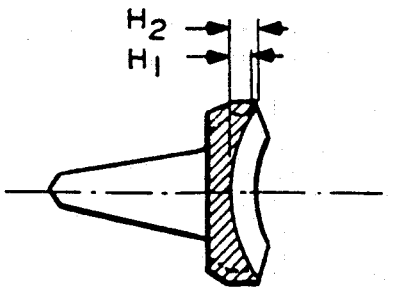

COMPOUND SHAPE ROTATING BEARING

This is a continuation of copending application Ser. No. 07/378,244 filed on Jul. 11, 1989, now abandoned.

BACKGROUND OF THE INVENTION

This invention has to do with orthopedic prosthetics. More specifically, this invention relates to prosthetic joints, and more particularly, to prostheses for replacement of dysfunctional knee joints.

Orthopedic prostheses of the type with respect to which the present invention is particularly useful are disclosed in our U.S. Pat. No. 4,309,778 for NEW JERSEY MENISCAL BEARING KNEE REPLACEMENT and U.S. Pat. No. 4,470,158 for JOINT ENDO PROSTHESIS. The subject matter of these patents is particularly relevant and is incorporated herein by reference.

Prostheses structured in accordance with the teachings of our prior patents have been singularly successful, particularly when used as knee replacements for dysfunctional knees. From time-to-time, however, the prostheses have been implanted with less attention to proper ligamentous tension than is necessary for proper operation. Under such circumstances, when certain loading conditions occur on the prosthesis, such as the loads experienced when the patient arises from a chair, subluxation can occur.

Considering initially a rotating bearing knee structure, according to U.S. Pat. No. 4,470,158, non-uniform loading often occurs when the patient moves from seated to a standing position. Typically, the stresses which are generated during movement from seated to a standing position tend to displace the distal femur anteriorly with respect to the proximal tibia. With the rotating bearing knee prosthesis in place, there are no cruciate ligaments and therefore there is no anterior-posterior stability independent of the prosthesis. If the prosthesis was implanted without proper attention to ligamentous tension, the introduction of medial lateral forces tending to cause varus-valgus torque may tend to lift one of the femoral condylar surfaces off the rotating bearing element. If the lift is sufficient to permit movement of the rotating bearing under the femoral condylar surface, then subluxation may occur.

With respect to meniscal bearing knee replacement of the type shown in U.S. Pat. No. 4,309,778, the problem is not so often observed because the medial and lateral bearing elements are not connected and a certain amount of cruciate ligamenture is maintained. However, shear stresses such as those attendant to moving from seated to standing position when coupled with varus-valgus torque which lifts one of the femoral condylar surfaces off the bearing element may also result in subluxation.

Obviously, with respect to either prosthesis construction, pure shear stresses of sufficient magnitude may be sufficient to cause subluxation. Ordinarily, such forces are directed anteriorly as a result of stresses occurring during natural but extreme flexion.

The occurrence of subluxation as a result of shear stresses is a problem which has been recognized in the field. One approach to reducing the occurrence of subluxation has been to provide posterior stabilization. Prostheses constructed pursuant to this approach utilize a spine formed on the tibially mounted bearing, which is intended to cooperate with a cam surface formed in the femoral element to reduce the likelihood of subluxation. It has been found, however, that the requirement to form a cavity in the femur to accomodate the design creates problesm, and flexion is limited such that the function of the prosthesis does not correspond to that of the natural joint. Further, the tibial spine element of such designs acts as a lever arm which tends to lift the tibial bearing off its platform by rotation. Even the stresses from normal activities create loads which may be unacceptable, sometimes contributing to loosening of the tibial element from the tibia itself.

It is an object of the present invention, therefore, to provide a bearing for an orthopedic prosthesis which reduces the likelihood of subluxation.

A further object of the present invention is to provide a joint prosthesis with at least one bearing element structured to reduce the likelihood of subluxation.

Yet another object of the present invention is to provide a bearing for a joint prosthesis which is useful with presently known joint prostheses.

SUMMARY OF THE INVENTION

These objects and others not enumerated are achieved by the bearing of the present invention, one embodiment of which may include a first bearing surface for engagement with the first surface of a first prosthesis element, a second bearing surface for articulation with a second surface of a second prothesis element, wherein the planform shape of said first bearing surface is dissimilar to the planform shape of said second bearing surface.

DETAILED DESCRIPTION OF THE DRAWIGS

A more complete understanding of the present invention may be had from the following detailed description, particularly when read in view of the accompanying drawings, wherein:

FIGS. 5 and 6 are anterior elevation views of the joint prosthesis of FIG. 1–4 showing displacement of one prosthesis element from a prior art bearing as a result of loose ligamenture and a valgus torque;

FIG. 7 is a plan view of a bearing structured according to the invention (solid lines) as compared with a known bearing shape (broken lines);

FIG. 8 is a side view, partly in section, of the bearing of FIG. 7;

FIG. 9 is a front view, partly in section, of the bearing of FIG. 7;

DETAILED DESCRIPTION

As stated above, this invention relates to orthopedic joint prosthetics. In particular, this invention relates to total knee prosthetics and bearings therefor. However, it will be recognized by those skilled in these arts that while a preferred embodiment of the invention is disclosed in the context of knee prosthetics, the invention is applicable as well to other joint prosthetics such as those for ankles, knuckles and the like.

In analyzing the present invention, it is useful briefly to review the basics regarding forces which occur in a knee prosthesis to cause subluxation. FIGS. 1 through 4 schematically depict a rotating platform knee prosthesis. The prosthesis includes a tibial element 12, a femoral element 14 and a platform bearing member 16.

Figure 1:
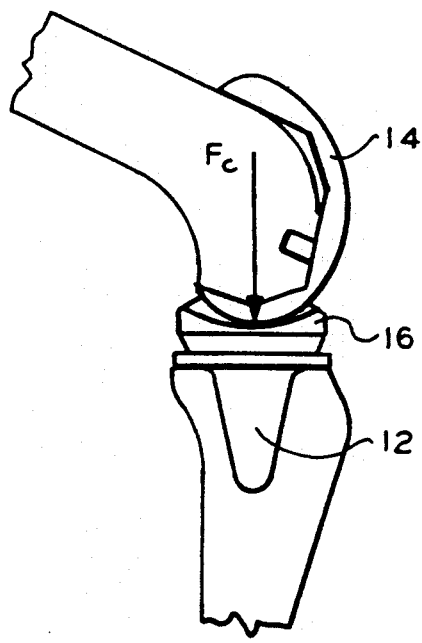
FIGS. 1–4 are side elevation views of a joint prosthesis incorporating a bearing according to the present invention under different stress load conditions through subluxation.
Figure 2:
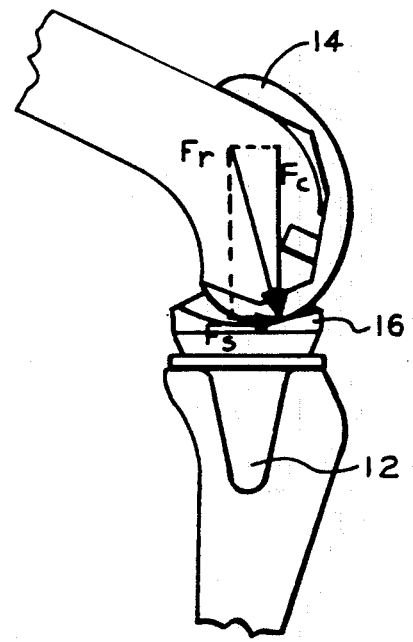
Figure 3:
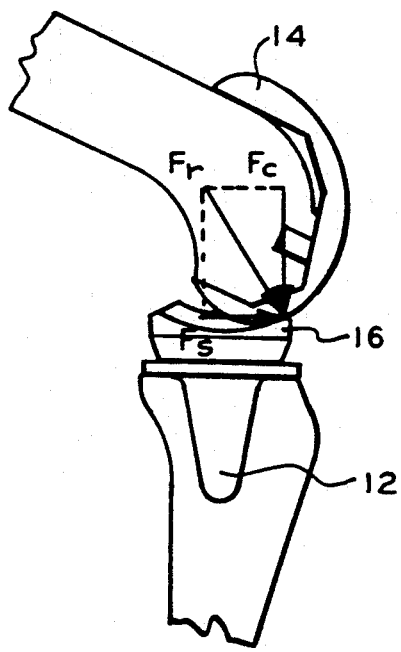
Figure 4:
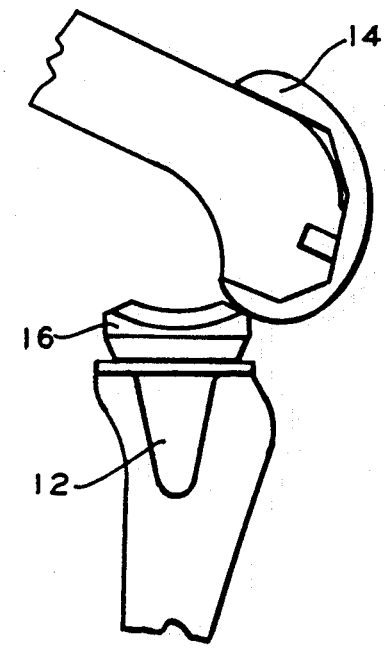

In the absence of shear forces tending to displace the elements in the anterior-posterior (AP) direction, the load on the bearing member 16, e.g., from the weight of the patient, generates a compressive force through the femoral element $F_c$ the vector of which is generally perpendicular to the interface as shown in FIG. 1. When a shearing force is introduced, e.g., by the patient moving from a sitting to a standing position or by reason of an outside force, a force vector $F_s$ is introduced in a direction generally parallel to the interface as is shown in FIG. 2. The combination of the two forces results in an effective resultant force $F_r$ acting through the condylar surfaces of the femoral element 14 on the surface of the bearing element 16. As is clear from the schematic, the shear force tends to displace the femoral component anteriorly.

Where the ratio of the shear force to compressive force component increases to a critical value, the resulting force Fr will displace the effective point of contact between the femoral element and the bearing element to the anterior edge of the bearing lip as is shown in FIG. 3. A further increase in this ratio resulting from either an increase in the shearing component and/or a decrease in the compressive component will produce subluxation as shown in FIG. 4.

The foregoing discussion is presented in the context of pure shearing forces. As a practical matter, very few subluxations occur as a result of pure shearing forces. Further, where the implanting surgeon has placed appropriate emphasis on maintaining proper ligamentous tension, the likelihood of subluxation as a result of pure shearing stresses or even shearing stresses coupled with varus or valgus stresses is remote.

However, where inadequate attention is given by the implanting surgeon to maintaining or establishing proper ligamentous tension, or where ligamentous laxity occurs for any other reason, a combination of bearing stress and stress generated by valgus or varus forces can increase the likelihood of subluxation.

Referring, therefore, to FIG. 5, there is shown an anterior view of knee implanted with a rotating platform knee prosthesis as described in detail in our U.S. Pat. No. 4,470,158. The lateral collateral (LC) ligament is shown in proper tension and the medial collateral ligament (MC) is shown to be loose, thus reflecting, for example, that insufficient attention was given the ligamenture during the implanting procedure.

Considering now FIG. 6, the same knee is shown being subjected to a valgus torque of sufficient magnitude to raise the medial condylar surface of the femoral component off the surface of the rotating bearing component to the level above the medial anterior lip of the bearing element. If, while the prosthesis is thus stressed, an anteriorly directed shear stress is introduced, the rotating bearing element will be caused to rotate such that while both the femoral condylar elements move anteriorly with the lateral side of the rotating bearing, the medial side of the rotating bearing moves posteriorly. If such rotation is sufficient to displace the condylar surface beyond the anterior bearing lip, subluxation occurs.

As is recognized by those skilled in these arts, bearing surfaces used in prosthetics, particularly knee prosthetics, have been given lower planform shapes which correspond generally to the shape of the tibial tray. In this regard, see generally the bearing insert 139 used with respect to tibial component 101 of the rotating bearing knee of our U.S. Pat. No. 4,470,158. Also, see the overall planform presented by the combined bearings 117 of the meniscal bearing knee replacement shown in our U.S. Pat. No. 4,309,778. Also, as will be recognized by those skilled in these arts, known bearing shapes have provided for upper bearing surface planforms which are substantially identical to the lower bearing planform. This appears to have been the generally accepted approach for two reasons.

First, the upper surface of the bearing element represents the substitute articular geometry of the tibia and thus the shape of this surface has been made to approximate the shape of the surface it replaces, i.e., the top surface of the tibia on which the tray is placed. Thus, the tray is shaped like the top of the tibia and the bearing is shaped like the tray so that it also approximates the shape of the top of the tibia.

Secondly, to make the planform of the upper bearing surface different from the planform of the lower bearing surface would cause the sidewalls connecting the upper and lower surfaces to be compound curves which are more difficult to machine than less complex shapes.

It has been found, however, that to provide an upper bearing surface which departs from the naturally occurring planform, i.e., the planform of the unresectioned proximal tibia, can produce several advantages which appear to outweigh any attendant machining difficulties.

For purposes of this specification, the term "planform" means the shape defined by the projection of the peripheral edge of a surface of the bearing on a plane disposed perpendicularly to the central axis of the bearing. As is evident from FIG. 9, the central axis of the bearing is the vertical axis about which the bearing rotates, i.e. the axis of rotation of the bearing. FIG. 7 presents the planforms of the bearing of FIGS. 7-9.

Referring therefore to FIG. 7, the planforms of the upper surfaces of knee prosthetic bearing components for a rotating platform joint are shown by way of comparison. The planform of the known bearing is shown in broken line and the planform of the improved bearing is shown in solid line. As is clear from the figure, the improved bearing is larger in planform area than the known bearing. In this regard, the size of the planform area of the upper surface of the improved bearing is limited only such as to not interfere with the soft tissue around the knee. Generally, a planform which is no larger in size than the planform of the distal femur is considered to be acceptable.

By taking advantage of the increased area, the height of engagement of the upper bearing surface can be increased, thus reducing the likelihood of subluxation. Referring to FIGS. 8 and 9, there is shown in sectional elevation a comparison of a bearing element with the prior art relationship between upper and lower bearing surface planform (see broken lines) and a bearing element structured in accordance with the present invention (solid lines). The known bearing element has a height of engagement $H_1$, where the bearing element of the present invention has a height of engagement $H_2$.

For purposes of this application, the term height of engagement means the vertical distance (FIG. 9) between the low point A of the generally concave upper bearing surface and the point B along the anterior edge of the upper bearing surface contained in a vertical anterior-posterior plane which passes through low point A. Thus, it can be said that point B is anteriorly adjacent to point A.

With specific reference to FIG. 9, the anteriorly adjacent high point for the prior art bearing configuration is shown as $B_1$. Accordingly, the height of engagement for the prior art bearing is the vertical distance between points A and $B_1$. Similarly, the anteriorly adjacent high point for the bearing of the present invention is shown as $B_2$. The height of engagement for the bearing of the invention is thus the vertical distance between points A and $B_2$.

For bearings of the type of the present invention a useful indicator of the ability to avoid subluxation is the ratio of the height of engagement to the width of the bearing. In the invention of our '158 patent, the height of engagement to width ratio is approximately 0.10. It has been found that the likelihood of anterior subluxation is significantly diminished where the ratio of anterior height of engagement to bearing width is 0.14 or greater.

The disadvantage of the compound shape of the bearing sidewall as required by the bearing of the present invention remains. However, modern computer-driven machine tools now allow the economical generation of such surfaces. Thus, one can exploit the benefits of an upper surface planform that is dissimilar from the lower surface planform without significantly increasing the manufacturing cost of the bearing.

Figure 10:
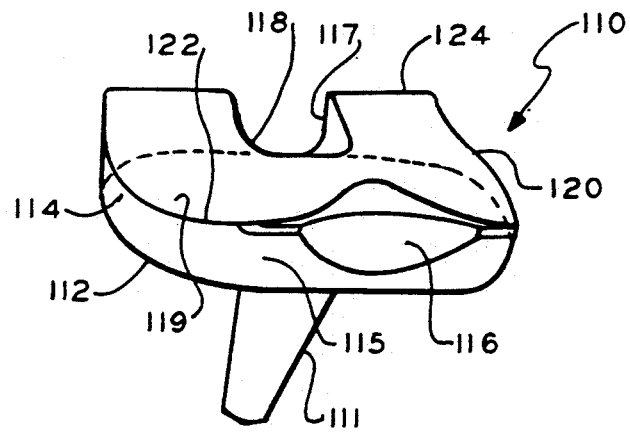
FIG. 10 is an isometric view of rotating platform bearing according to the present invention.
Figure 11:
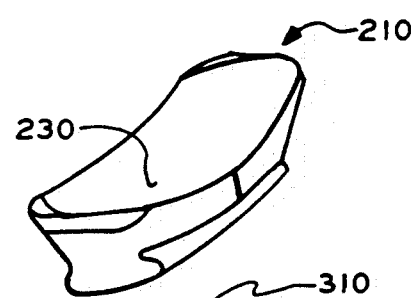
FIG. 11 is an isometric view of a meniscal bearing according to the present invention.

Two embodiments of bearings according to the present invention are depicted in FIGS. 10 and 11. Referring to FIG. 10, a bearing according to the present invention and suitable for use with the rotating platform bearing joint replacement shown in our U.S. Pat. No. 4,470,158 is designated generally by the reference numeral 110. Bearing 110 includes a tapered shaft 111, a bottom surface 112 which is structured to be received and to articulate within a tibial tray of the type disclosed in the '158 patent, sidewall 114 of a compound shape, a front wall 115 having a recess 116 formed therein, back wall 117 having a recess 118 formed therein, and an upper or upwardly facing surface 119 having a peripheral edge 120 which defines a planform corresponding to the shape of the distal end of the femoral component with which it articulates. Recess 116 is used to provide clearance between the bearing 110 and a patella component, or patella (not shown), and the patella tendon. Recess 118 is provided to permit clearance for the posterior cruciate ligament which, if retained, can help stabilize the knee.

Figure 14:
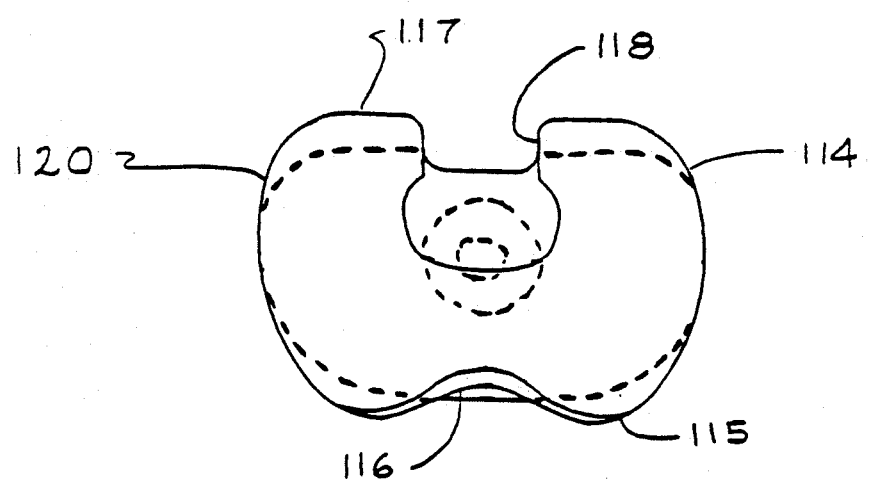
FIG. 14 is a plan view of the bearing of FIG. 10.

As best may be seen in FIG. 14 which shows the planform of the upper surface of bearing 110 in solid line and the planform of the lower surface of bearing 110 in broken lines, the planforms are dissimilar in accordance with the invention. Specifically, the planform of the lower surface of bearing 110 defines a smaller area of more regular shape than the planform of the upper surface, which is a more complex curve.

The height of the anterior superior edge 122 of the upper surface of bearing 110 is greater than the height of the posterior superior edge 124 for two reasons. First, increasing the height of the posterior edge would reduce the flexion permitted by the bearing since, in deep flexion, it would engage the shaft of the femur earlier than desired. Secondly, dislocations typically occur by the femoral component passing over the anterior edge. Thus, less posterior dislocation resistance is needed.

The maximum anterior height of engagement to width ratio of 0.10 used for the bearing disclosed in the '158 patent was found insufficient to compensate for surgical ligamenture error to prevent anterior subluxation. The bearing of the present invention has an anterior height of engagement to width ratio of 0.20 as a result of modifying the planform shape of the upper bearing surface to extend the wall, thereby permitting an increase of the height of that wall. The posterior ratio was increased but only to a level of 0.16 since, as discussed above, further increase would have had a detrimental effect on the flexion capabilities of the prosthesis. Further, as a practical matter, increasing the posterior ratio would make the prosthesis more difficult to implant since the femoral component must clear the posterior edge of the upper bearing surface during implantation.

Disclosed in FIG. 11 is a meniscal bearing 210 structured according to the present invention, which is suitable for use with the meniscal bearing knee replacement disclosed in U.S. Pat. No. 4,340,978 (the '978 patent).

The improved meniscal bearing disclosed in FIG. 11 is similar in all respects to the meniscal bearing disclosed in the '978 patent, except that the planform of the upper surface of the bearing is larger and the height of the anterior and posterior edges of the upper surface are greater.

Figure 12:
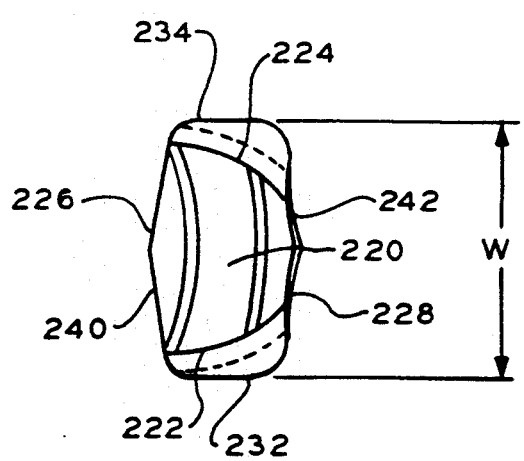
FIG. 12 is a bottom view of the bearing of FIG. 11.

Referring specifically to FIG. 12, which is a bottom view of the bearing of FIG. 11, there is shown the planform of both the lower and upper bearing surfaces of bearing 210. Additionally, there is shown in broken lines the planform of the upper surface of a prior art bearing.

Lower bearing surface 220 can be seen to be defined by anterior edge 222 and posterior edge 224 together with medial and lateral edges 226 and 228 respectively. Similarly, the planform of upper bearing surface 230 can be seen to be defined by anterior edge 232 and posterior edge 234 together with medial and lateral edges 226 and 228. The increased upper bearing surface area of the improved bearing element is clearly evident from a comparison of the planform of the upper bearing surface of the prior art bearing component (broken line) to that of the improved component (solid line) further, it is clear that the planform shapes of the upper and lower surfaces of the bearing are dissimilar.

Thus, the planform shape of the upper surface of the bearing is larger and corresponds more to the planform shape of the distal femur than the planform shape of the proximal tibia.

In the bearing of the '778 patent, the maximum height of engagement to width ratio is 0.095, whereas in the present invention the height of engagement to width ratio for the bearing of FIG. 11 has been increased to 0.14.

The utility of the concepts described herein are particularly applicable to congruent type bearings as disclosed in the '978 and '158 patents, since the engagement possible with such bearings is substantially greater than that possible with incongruent bearings of the prior art.

It should also be recognized that subluxation has been a relatively rare occurrence with respect to the knee prosthetic structures shown in the '978 and '158 patents.

However, the change in shape of the upper surface of the bearing of the present invention and the attendant increase in clearing edge height and height of engagement to width ratios should essentially eliminate subluxation as a clinical problem. The improved stability of congruent bearings should therefore eliminate the need for posterior stabilized bearings and related approaches with their large femoral bone resection and surgical complexity.

Figure 13:
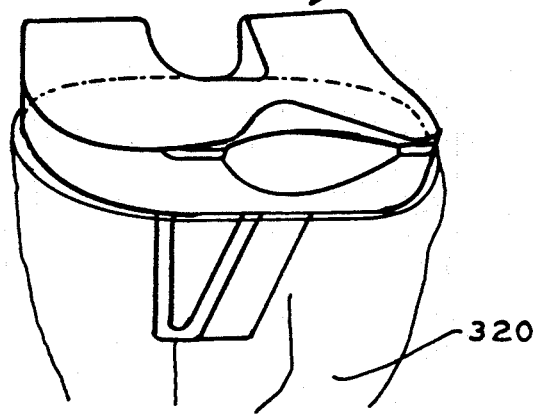
FIG. 13 is an isometric view of a bearing according to the present invention as used directly in contact with the proximal tibia.

Finally, the improved bearing element according to the present invention may be mounted directly on a tibia. Thus FIG. 13 shows a bearing 310 according to the invention mounted on a tibia 320. The head of the tibia is prepared by surgically providing a flat surface on the proximal tibia and mounting bearing 310 therein. The operation of the prosthesis in conjuntion with a femoral element as described above will provide all the benefits of the invention as described above.

It will be recognized by those skilled in these arts that the embodiments shown are preferred and illustrative. Many modifications and variations to the preferred and illustrative embodiment may be made without departing from the spirit and scope of the invention.

What we claim is:

1. An improved prosthetic joint including:
   a first element for attachment to a first bone, said first element having a first substantially flat surface for facing generally away from said first bone;
   a second element for attachment to a second bone, said second element having a second surface for facing generally away from said second bone; and
   bearing means disposed between said first and second elements, said bearing means having a central axis and being defined by first and second opposed surfaces spaced apart with respect to the central axis, said first bearing surface being substantially flat and having a portion in contact with said first substantially flat surface of said first element, at least a portion of said second bearing surface being in contact with said second surface of said second element;
   wherein the area of the planform shape defined by the projection of the peripheral edge of the first surface of said bearing means on a plane disposed perpendicular to said central axis of said bearing means is smaller than and dissimilar to the area of the planform shape defined by the projection of the peripheral edge of the second surface of said bearing means on a plane disposed perpendicular to said central axis of said bearing means.

2. An improved prosthetic joint according to claim 1 wherein said second surface of said learing means includes a generally concave portion having an anterior edge and a posterior edge and wherein the height of engagement of the anterior edge is greater than the height of engagement of the posterior edge as measured in the anterior-posterior plane containing the low point of said generally concave portion.

3. An improved prosthetic joint according to claim 1 wherein said bearing is a rotating platform-type bearing and wherein said second surface includes a generally concave portion having an anterior edge and a posterior edge and wherein the ratio of the height of engagement of the anterior edge to the medial-lateral width of the bearing across the second surface of the bearing is at least 0.18.

4. An improved prosthetic joint according to claim 1 wherein said bearing is a meniscal type bearing and wherein said second surface of said bearing includes a generally concave portion having an anterior and a posterior edge and wherein the ratio of the height of engagement of the anterior edge to the medial-lateral width of the bearing across the second surface of the bearing is at least 0.12.

5. A bearing for a prosthetic joint for articulating a first bone and a second bone, said bearing being defined by first and second opposed surfaces spaced apart with respect to a central axis, said first bone having a surface surgically formed therein to engage at least a portion of said first surface of said bearing, said second surface having at least a portion for engagement with a surface of a joint element mounted on said second bone for articulation with said surface of said joint element, wherein the planform shape shape defined by the projection of the peripheral edge of said first surface of said bearing on a plane disposed perpendicular to said central axis of said bearing is dissimilar to and its area is smaller than the planform shape defined by the projection of the peripheral edge of said second surface of said bearing on a plane disposed perpendicular to said central axis of said bearing.

6. A bearing according to claim 5 wherein said second surface of said bearing includes a generally concave portion having an anterior edge and a posterior edge and wherein the height of engagement of the anterior edge is greater than the height of engagement of the posterior edge as measured in the anterior-posterior plane containing the low point of said generally concave portion.

7. A bearing according to claim 5 wherein said second surface of said bearing includes a generally concave portion having an anterior edge and a posterior edge and wherein the ratio of the height of engagement of the anterior edge to the medial-lateral width of the bearing across the second bearing surface is at least 0.18.

8. A bearing for a prosthetic joint, said prosthetic joint including a first element for being secured to a first bone and having a first surface, a second element for being secured to a second bone and having a second surface, and a bearing being defined by first and second opposed surfaces spaced apart with respect to a central axis, the first surface of the bearing facing said first surface of said first element at least a portion of which engages said first surface of said first element, said second surface of the bearing facing said second surface of said second element at least a portion of which engages said second surface of said second element, and
   wherein the planform shape defined by the projection of the peripheral edge of the first surface of said bearing on a plane disposed perpendicular to said central axis of said bearing is smaller in area than and dissimilar to the planform shape defined by the projection of the peripheral edge of the second surface of said bearing on a plane disposed peripendicular to said central axis of said bearing.

9. A bearing according to claim 8 wherein said second surface of said bearing includes a generally concave portion having an anterior edge and a posterior edge and wherein the height of engagement of the anterior edge is greater than the height of engagement of the posterior edge as measured in the anterior-posterior plane containing the low point of said generally concave portion.

10. A bearing according to claim 8 wherein said bearing is a rotating platform-type bearing and wherein said second surface of said bearing includes a generally concave portion having an anterior edge and a posterior edge and wherein the ratio of the height of engagement of the anterior edge to the medial-lateral width of the bearing across the second bearing surface is at least 0.18.

11. A bearing according to claim 8 wherein said bearing is a meniscal type bearing and wherein said second surface of said bearing includes a generally concave portion having an anterior and a posterior edge and wherein the ratio of the height of engagement of the anterior edge to the medial-lateral width of the bearing across the second surface of the bearing is at least 0.12.

* * * * *